(12) United States Patent
Perin et al.

(10) Patent No.: US 6,210,344 B1
(45) Date of Patent: Apr. 3, 2001

(54) METHOD AND APPARATUS FOR PASSIVE HEART RATE DETECTION

(75) Inventors: Dino Perin, New Palestine; Richard A. Riedel, Carmel, both of IN (US)

(73) Assignee: UMM Electronics, Inc., Indianapolis, IN (US)

( * ) Notice: Subject to any disclaimer, the term of this patent is extended or adjusted under 35 U.S.C. 154(b) by 0 days.

(21) Appl. No.: 09/275,853

(22) Filed: Mar. 24, 1999

(51) Int. Cl.$^7$ .................................................. A61B 5/02
(52) U.S. Cl. ........................................................ 600/528
(58) Field of Search .................... 600/528, 502, 600/513

(56) References Cited

U.S. PATENT DOCUMENTS

| | | |
|---|---|---|
| 3,132,208 | 5/1964 | Dymski et al. |
| 3,182,129 | 5/1965 | Clark et al. |
| 3,233,041 | 2/1966 | Croslin . |
| 3,247,324 | 4/1966 | Cefaly et al. |
| 3,348,535 | 10/1967 | Gregg . |
| 3,790,712 | 2/1974 | Andries . |
| 3,799,147 * | 3/1974 | Adolph et al. ................... 600/528 |
| 3,989,895 * | 11/1976 | O'Daniel, Sr. .................. 600/528 |
| 4,195,642 | 4/1980 | Price et al. . |
| 4,220,160 | 9/1980 | Kimball et al. ................. 128/715 |
| 4,248,244 | 2/1981 | Charnitski et al. ............. 128/706 |
| 4,295,472 | 10/1981 | Adams ............................ 128/690 |
| 4,362,164 | 12/1982 | Little et al. .................... 128/639 |
| 4,378,022 * | 3/1983 | Suobank et al. ................ 600/528 |
| 4,420,000 | 12/1983 | Bailey ............................. 128/706 |
| 4,528,689 | 7/1985 | Katz ................................. 381/67 |
| 4,586,514 | 5/1986 | Schlager et al. ................ 128/773 |
| 4,592,365 | 6/1986 | Georgi ............................ 128/680 |
| 4,598,417 | 7/1986 | Deno ................................ 381/67 |
| 4,618,986 | 10/1986 | Hower .............................. 381/67 |
| 4,720,866 | 1/1988 | Elias et al. ...................... 381/67 |
| 4,792,145 | 12/1988 | Eisenberg et al. .............. 128/715 |
| 4,972,841 * | 11/1990 | Iguchi ............................. 600/528 |
| 5,010,889 | 4/1991 | Bredesen et al. ............... 128/715 |
| 5,213,108 | 5/1993 | Bredesen et al. ............... 128/715 |
| 5,218,969 | 6/1993 | Bredesen et al. ............... 128/710 |
| 5,337,753 | 8/1994 | Lekhtman ....................... 128/706 |
| 5,467,775 | 11/1995 | Callahan et al. ................ 128/715 |
| 5,539,831 | 7/1996 | Harley ............................. 381/67 |
| 5,602,924 | 2/1997 | Durand et al. ................... 381/67 |
| 5,727,561 | 3/1998 | Owsley ............................ 128/691 |
| 5,774,563 | 6/1998 | DesLauriers et al. .......... 381/67 |
| 5,795,300 | 8/1998 | Bryars ............................. 600/500 |
| 5,807,267 | 9/1998 | Bryars et al. ................... 600/500 |
| 5,812,678 | 9/1998 | Scalise et al. .................. 381/67 |
| 5,825,895 | 10/1998 | Grasfield et al. ............... 381/67 |
| 5,832,093 | 11/1998 | Bernstein et al. .............. 381/67 |
| 5,841,846 | 11/1998 | Abbruscato .................... 379/106 |
| 5,844,995 | 12/1998 | Williams ......................... 381/67 |
| 5,844,997 | 12/1998 | Murphy, Jr. .................... 381/92 |

\* cited by examiner

*Primary Examiner*—William E. Kamm
(74) *Attorney, Agent, or Firm*—Woodard, Emhardt, Naughton, Moriarty & McNett

(57) ABSTRACT

A method and apparatus for measuring the heart rate of a patient. In one embodiment the apparatus includes a hollow bell mounted on a diaphragm. A transducer element is also positioned therein to receive sound transmitted through the diaphragm, convert the sounds into electrical impulses, and transmit the electrical impulses to a microprocessor. The electrical impulses have real-time wave patterns corresponding to the real-time wave patterns of the original sounds. The microprocessor performs mathematical operations on wave pattern data conveyed by the electrical impulses to determine a numerical value corresponding to the frequency of the wave patterns. This numerical value is sent to a digital output and displayed thereon.

23 Claims, 3 Drawing Sheets

METHOD AND APPARATUS FOR PASSIVE HEART RATE DETECTION

TECHNICAL FIELD OF THE INVENTION

The present invention relates generally to the field of acoustics, and more specifically to an electronic apparatus for the passive detection of a patient's heart rate.

BACKGROUND OF THE INVENTION

The heart rate is one of the most basic life signs of a patient. It is very important for a physician or other health care provider to have quick and accurate heart rate information when treating a patient, especially in an emergency situation. One time-honored method of obtaining the heart rate of a patient is by the auscultation and/or palpitation method, wherein the doctor, nurse, or other trained health care professional is required to feel or listen for a pulse, count the heart beats for a fixed period of time, and then calculate the pulse rate. One very familiar listening tool used for auscultation is the stethoscope. While providing the human touch, the auscultation and palpitation techniques are particularly prone to human error and further require the caregiver to focus on a counting task instead of the immediate needs of the patient. In an emergency situation, a doctor's time can be much better spent if he doesn't have to take time out to count the patient's pulse rate.

Another common technique for measuring a patient's pulse rate is by using electronic instrumentation. The heart rate may be detected by measuring rhythmic changes in the EMF potential generated by the periodic firing of the neurons of the cardiac system (electrocardiogram or ECG), by measuring vascular pressure changes coincident with the expanding and contracting of blood vessels with the heart beat (sphygmometer), and/or by measuring the changes in the Doppler shift of ultrasonic energy caused by the changes in the relative speeds of red blood cells reflecting the ultrasonic energy back at its source (Doppler ultrasound stethoscope or DUS). While more accurate than auscultation and palpitation, the above-mentioned instrumentation capable of performing these measurements tend to be bulky and cumbersome, and also require special preparations be made before measurements may be taken. Moreover, in the case of the ECG, specialized training is required to both administer the tests and to interpret the results. ECG monitors are thus found primarily in controlled clinical settings.

Currently, a patient's heart rate is either mechanically assessed in a clinical setting by bulky and expensive equipment or manually assessed in the field by a human caregiver. There remains a need for a method and apparatus for the measurement of heart rate in the field that does not require the caregiver to focus on the task of measuring the heart rate to the exclusion of other, potentially more important, tasks. The present invention satisfies this need.

SUMMARY OF THE INVENTION

The present invention relates to a method and apparatus for measuring the heart rate of a patient. One form of the present invention includes a stethoscope having a hollow bell or cone chamber with a diaphragm for sound pickup. A transducer element is positioned within the bell chamber and operationally connected to a microprocessor. The transducer converts sound energy in the bell to electrical energy signals having the same patterns as the original sounds, and sends the electrical signals to the microprocessor. The microprocessor mathematically processes the electrical signals and produces an output signal corresponding to the frequency of the input signals. The output signal is numerically displayed on a screen.

One form of the present invention contemplates a combination, comprising: a stethoscope; a transducer operationally coupled to the stethoscope and adapted to convert sound impulses received by the stethoscope into electrical output impulses; a microprocessor adapted to receive the electrical output impulses from the transducer and further adapted to produce an microprocessor output signal; and a visual display adapted to receive and display the microprocessor output signal.

Another form of the present invention contemplates a combination, comprising: a sound pickup portion; a microprocessor operationally coupled to the sound pickup portion; and a visual display portion operationally coupled to the microprocessor; wherein the sound pickup portion is adapted to generate a first output signal; wherein the microprocessor is adapted to process the first output signal from the sound pickup portion and calculate a rate of rhythmic sounds; wherein the microprocessor is further adapted to produce a second electrical output signal corresponding to the rate to rhythmic sounds from the sound pickup portion; and wherein the visual display portion is adapted to display an output number corresponding to the second electrical output signal from the microprocessor.

Still another form of the present invention contemplates a method, comprising the steps of: placing a diaphragm coupled to a bell chamber against a patient's chest; amplifying the sound of the patient's heart beat in the bell chamber; channeling a portion of the sound energy to a microprocessor; counting the beats; calculating the rate of the beats; producing an electrical output signal corresponding to the calculated rate; and displaying the rate numerically.

One object of the present invention is to provide an improved passive heart rate monitor. Related objects and advantages of the present invention will be apparent from the following description.

DETAILED DESCRIPTION OF THE PREFERRED EMBODIMENT

Figure 1:
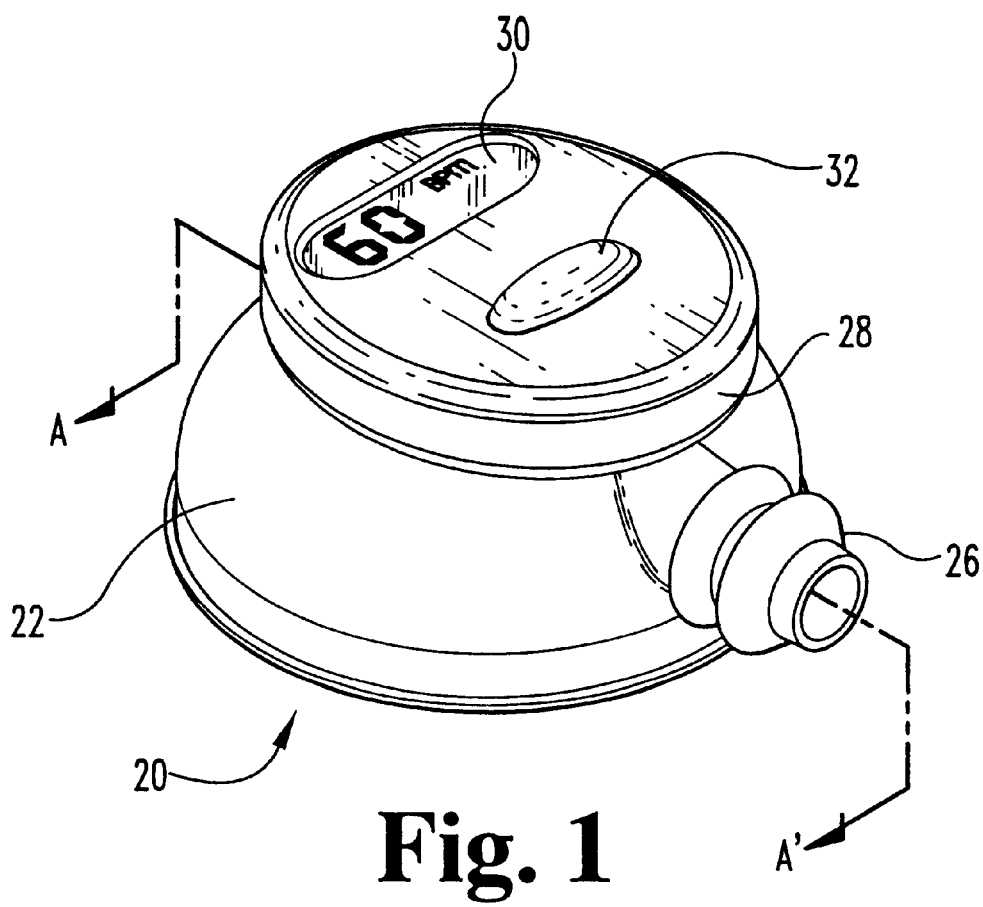
FIG. 1 is a perspective view of the preferred embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The stethoscope is a simple and familiar tool of the medical profession. The stethoscope is commonly found hanging around the health care provider's neck and operates by amplifying a patient's heart beat or other critical internal sounds and transmitting them through to the health care provider through earphones. The sound pickup is usually a hollow bell with a relatively flat diaphragm portion for contact with the patient's body. The diaphragm picks up the sound for the hollow bell to amplify. One or more hollow flexible tubes acoustically connect the bell to one or more earphones that are worn by the health care provider.

Another somewhat more sophisticated and somewhat less portable tool of the medical profession is the heart rate monitor. A typical heart rate monitor operates by measuring the changes in electromagnetic field (EMF) potential characteristic of the cardiac control function of the sympathetic nervous system. The heart is controlled by the routine and rhythmic firing of certain nerves of the sympathetic nervous system. Electrocardiograph (ECG) instrumentation can detect the rhythmic changes in nervous potential through electrodes attached to the exterior of the human body. The output signal so measured is the familiar PQRST waveform of the heart's beating action. The heart rate is obtained from the charting of the PQRST wave.

Alternatively, the heart rate may be measured by the sphygmometer, a device that measures the force and frequency of the pulse by detecting pressure changes in the circulatory system. A sphygmometer may include a pressure cuff or a pressure sensor that can be clamped onto a finger. The pulse is usually read as an analog output. The pulse rate is determined by counting the number of analog pulses for a given time period. While the sphygmometer can detect pulse rate, it is not as well suited for generating data regarding the regularity or normality of the heartbeat.

Another instrument that may be used to generate heart rate data is the Doppler ultrasound stethoscope (DUS). The DUS sends an ultrasonic signal at a frequency of several megahertz downstream a blood vessel along the direction of the blood flow. Some of the sound is reflected back to the transducer from moving blood cells and is frequency shifted according to their speed. The difference in frequency between the transmitted and reflected signals is produced as an audible tone proportional to the rate of blood flow. The rapid changes in the speed of the blood flow accompanying caused by the heart's beating action are heard as rhythmic changes in the tone. The heart rate may be determined from counting those changes.

Of the above-discussed instrumentation, the ECG unit produces the most accurate heart rate information. However, ECG machines are usually bulky and do not readily lend themselves to the quick determination of a patient's heart rate. In fact, the process of attaching the electrodes and taking a reading takes several minutes in the relatively sedate examination room setting. Moreover, the analysis of the PQRST wave is rather intricate and its interpretation requires a trained specialist.

The sphygmometer and the DUS both require manual counting and are thus both prone to manual counting error as well as the monopolization of the physician's time and attention while the heart rate is determined. Moreover, the DUS requires a gel-media interface between the ultrasound transducer and the patient and alignment of the transducer with a blood vessel.

The time honored, albeit low-tech, methods for measuring a patient's heart rate do not necessitate bulky specialized machinery but instead require the focused attention of the health care provider. A health care provider can manually determine heart rate by auscultation (listening to the heart beat/pulse and counting the number of beats in a fixed time) or palpitation (feeling the pulse and counting the number of beats in a fixed time). Both of these methods require the focussed attention of the health care provider while the counting is done, during which time no medical aid is given. In an emergency situation, immediate aid may be critical. However, the patient's heart rate might also be a critical piece of information required by the health care provider as necessary for providing proper aid.

Furthermore, the palpitation and auscultation methods are not as accurate as the mechanically determined techniques and are more prone to operator error. Moreover, conditions such as an irregular heartbeat are more difficult to detect and even more difficult to quantify by auscultation or palpitation.

The present invention combines the convenience and portability of the stethoscope with the mechanical accuracy of the mechanical instrumentation to provide a tool for the quick and accurate automated measurement of a patient's heart rate. The present invention allows the health care provider to focus their attention on the immediate needs of the patient while still obtaining the necessary heart rate information.

FIG. 1 illustrates the preferred embodiment of a stethoscope bell having a built-in passive heart rate detector 20. The passive heart rate detector 20 includes a bell or cone portion 22 mounted to a diaphragm portion 24. Diaphragm portion 24 is preferably relatively flat and acts as the base of bell portion 22. Bell portion 22 also includes an acoustic connector 26. A housing 28 is connected atop bell 22. Housing 28 includes a display 30 and an activation control 32.

Figure 2:
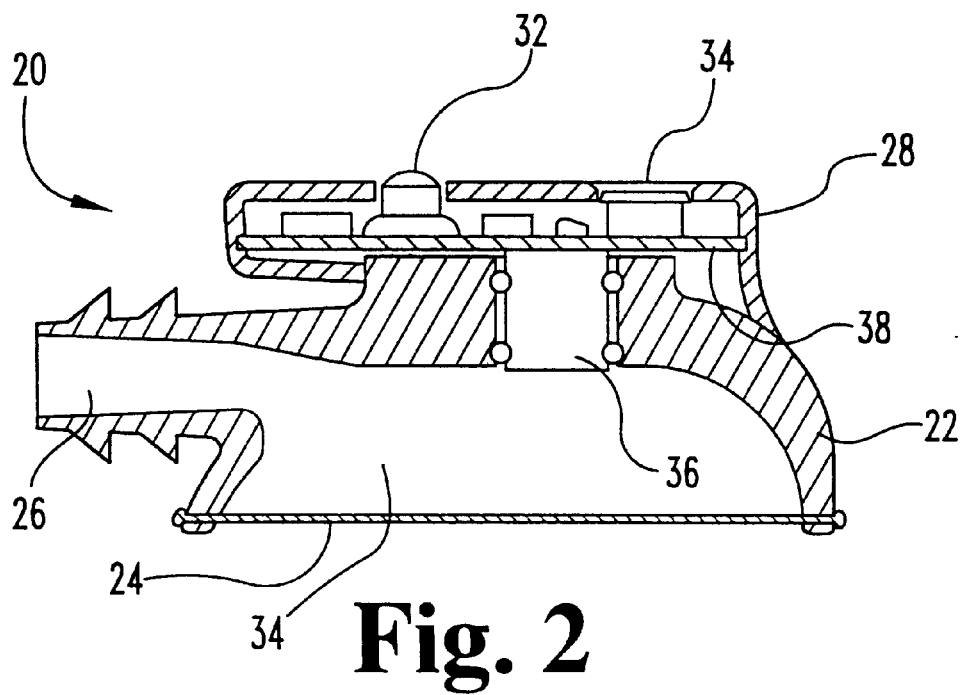
FIG. 2 is a sectional view of the embodiment of FIG. 1 taken along line A–A'.

FIG. 2 shows the interior of heart rate detector 20. The bell portion 22 and diaphragm 24 define a bell chamber 34. Sound entering through diaphragm 24 is amplified by chamber 34 and sent to a listener through acoustic connector or stem 26 and/or is converted to electrical impulses by transducer 36. Transducer 36 is mounted within chamber 34, and is also operationally coupled to microprocessor 38. Transducer 36 converts incident sound wave patterns into electrical impulses having the same wave patterns. Transducer 36 then provides the electrical impulses as an input for microprocessor 38. Microprocessor 38 is mounted within housing 28, and is connected to battery 40, actuator control 32, transducer 36, and display 30. Electrical impulses received from transducer 36 provide real time wave pattern data for microprocessor 38 to operate upon. Upon actuation, microprocessor 38 performs mathematical operations on the data to transform real time wave patterns into frequency data. The frequency data is provided as a numerical output for the display unit 30.

Figure 3:
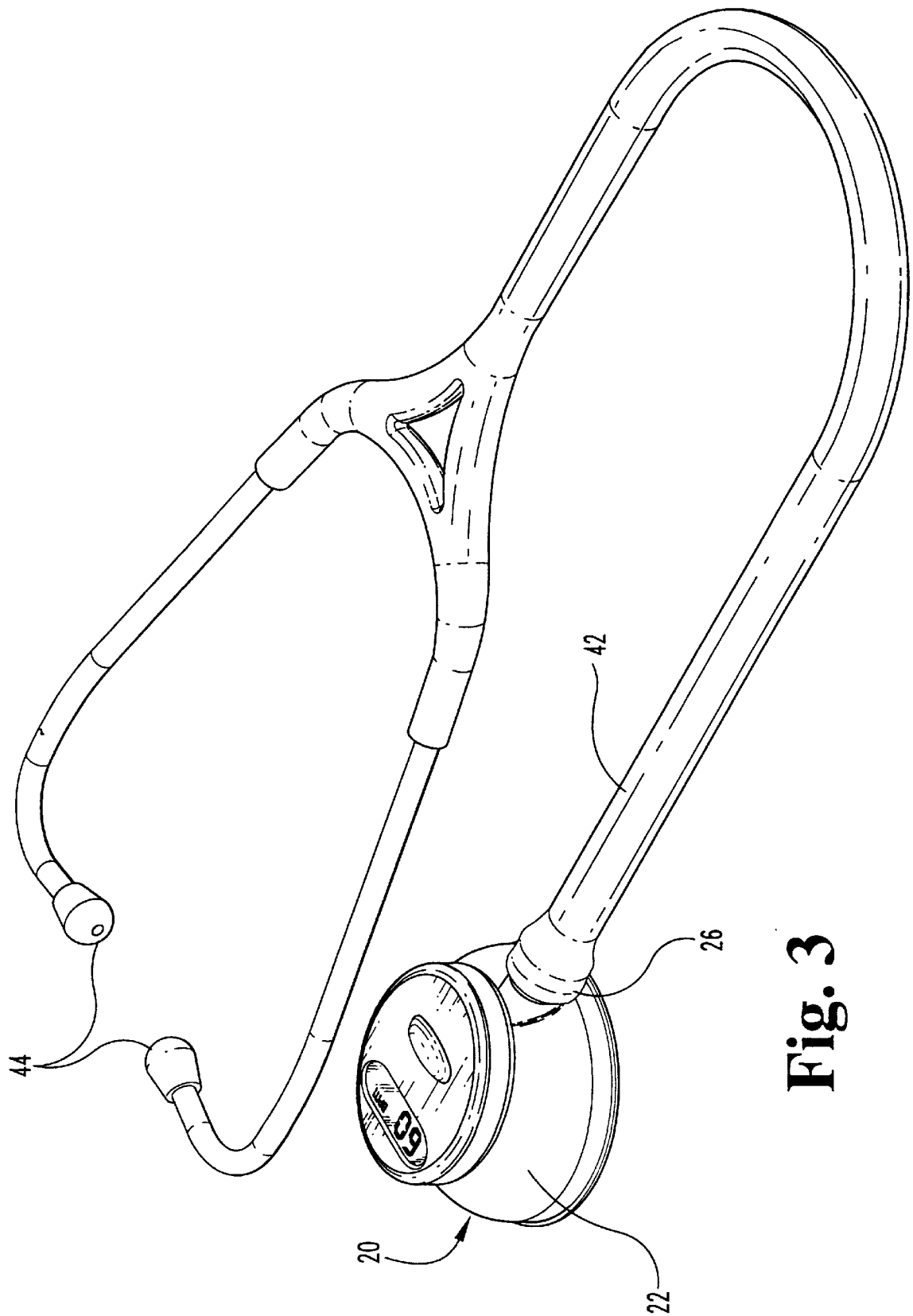
FIG. 3 is a view of FIG. 1 coupled to binaural earphones.

FIG. 3 illustrates a form of the present invention including acoustic tubing 42 connecting binaural earphones 44 to the bell chamber 34. Tubing 42 is flexible and transmits sound from chamber 34 to the earphones 44. Tubing 42 is connected to bell chamber 34 at stem 26.

Figure 4:
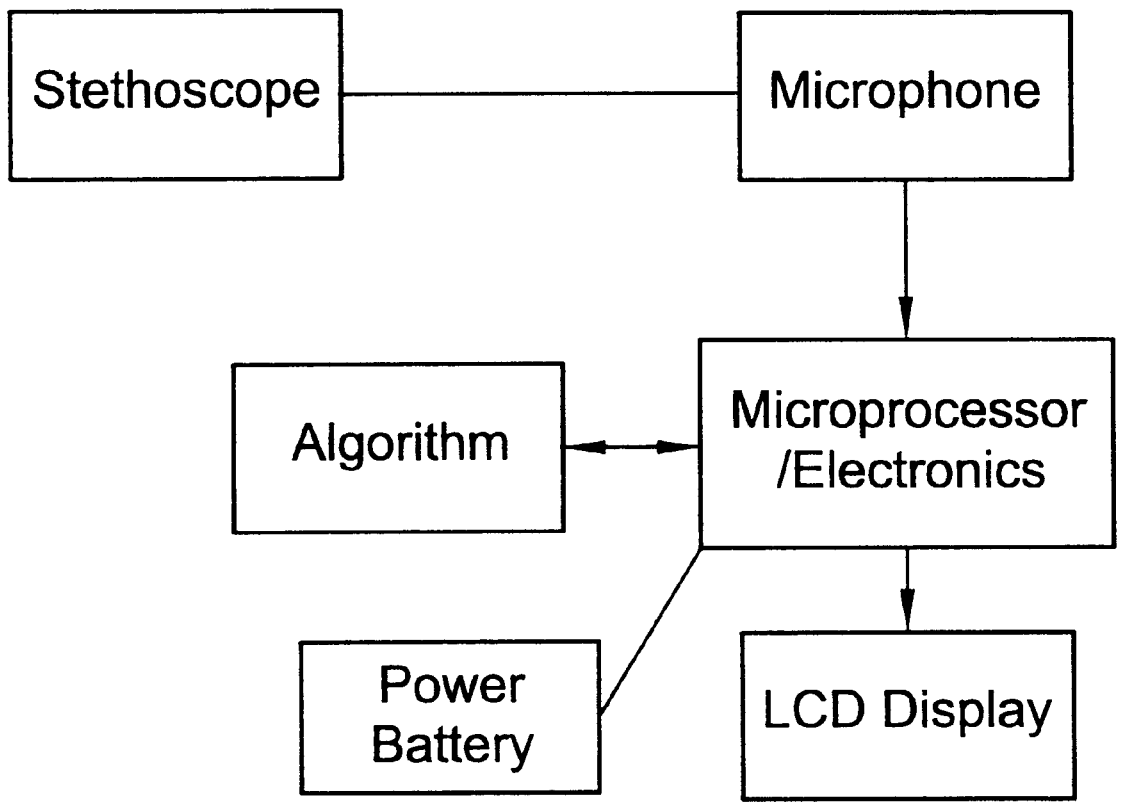
FIG. 4 is a flowchart illustrating the method of passive detection of heart rate.

FIG. 4 is a block diagram illustrating the operational process of the present invention. In operation, heartbeat sounds enter bell portion 22 of heart rate detector 20 through diaphragm 24 placed against the patient's chest. The heartbeat sounds are isolated and amplified in bell chamber 34. The heartbeat sound patterns are converted into corresponding electrical patterns by transducer 36 and sent to microprocessor 38. The electrical patterns correspond to the real time waveforms of the sounds picked up by the stethoscope. Microprocessor 38 performs a Fourier transform on the electrical patterns to decompose the waveforms into frequency and energy values. Microprocessor 38 extracts frequencies from a range of about 0.5 to 5.0 Hz as representing the heart beat, based on the calculated frequencies and corresponding energies. It is expected that if diaphragm 24 is properly situated over patient's heart, the heart beat sound component of the signal will be much greater than the background component in the 0.5 to 5.0 Hz range. Microprocessor 38 calculates the heart rate from the frequency data obtained from a signal sample taken for a predetermined length of time. Microprocessor 38 then sends a numerical output signal to display 30 corresponding to the heart rate.

One form of the present invention is contemplated as having microprocessor 38 sufficiently powerful and loaded with software capable of distinguishing between various types of heart beat abnormalities (based upon a comparison with known abnormal heartbeat patterns) and displaying the same. The heartbeat sound pattern is comprised of the sounds of all of the individual heart valves opening and closing and the heart chambers being filled and emptied. It is well known that these heart activities are also represented by the PQST wave patterns generated electrically by the firings of cardiac neurons and mapped by the ECG. The shape and timing of the electrical patterns generated by microprocessor 38 from the heartbeat sound patterns may be compared to preselected PQST patterns for regular heartbeat patterns as well as to preselected PQST patterns for such irregularities as heart murmur, irregular rhythm, incomplete valve closure, cardiac arrest, and the like. Microprocessor 38 can be adapted to store Fourier transforms characteristic of one or more types of abnormal heartbeat patterns and to compare them to the Fourier transform of the heartbeat sounds from the patient. The degree of matching necessary to flag a heartbeat as abnormal may be preselected (hardwired) or may be variable. When microprocessor 38 flags a heartbeat pattern as abnormal a message is displayed on display 30, alerting the health care provider that the heartbeat is abnormal and what, if any, known type of abnormal pattern was matched.

Another form of the invention is contemplated as having a microprocessor 38 adapted to extract frequencies characteristic of other bodily functions, such as respiration or the like.

Bell portion 22 of the preferred embodiment of the present invention may be formed from stainless or surgical steel, plastic, resin or any other structural material having adequate sound conduction properties. Diaphragm portion 24 may be formed from epoxy resin, steel, plastic or any convenient material having adequate sound conduction properties. Transducer element 36 may be formed from any convenient monolithic, stacked or composite ceramic or polymeric or combination piezoelectric material having sufficient sensitivity. Display unit 30 may be a liquid crystal screen or the like.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An analytical apparatus, comprising:
    a stethoscope;
    a transducer operationally coupled to the stethoscope and adapted to convert heartbeat sound impulses received by the stethoscope into electrical output impulses;
    a microprocessor electrically connected to the transducer and adapted to receive the electrical output impulses from the transducer and further adapted to produce an microprocessor output signal; and
    a visual display electrically connected to the microprocessor and adapted to receive and display the microprocessor output signal.

2. The apparatus of claim 1 further comprising a power source operationally coupled to the microprocessor and to the visual display.

3. The apparatus of claim 1 further comprising an activation control mounted on the stethoscope and electrically connected to the microprocessor and to the visual display, wherein actuation of the activation control initiates the microprocessor to produce an output signal and the visual display to display the output signal.

4. The apparatus of claim 1 wherein the visual display is a liquid crystal.

5. The apparatus of claim 1 wherein the microprocessor is further adapted to decompose the electrical impulses received from the transducer into frequency values, to extract heartbeat frequencies from a predetermined frequency range, and to produce an output signal corresponding to the heartbeat frequency values extracted from the predetermined frequency range.

6. The apparatus of claim 5 wherein the predetermined frequency range is from about 0.5 Hz to 5.0 Hz.

7. The apparatus of claim 5 wherein the microprocessor output signal corresponds to the heart rate.

8. The apparatus of claim 1 further comprising a stem coupled to the stethoscope and adapted to acoustically connect the stethoscope to an earphone.

9. The apparatus of claim 1 further comprising:
    a power source operationally coupled to the microprocessor and to the visual display;
    an activation control mounted on the stethoscope and operationally connected to the microprocessor;
    an earphone; and
    a stem acoustically connected between the stethoscope and the earphone;
    wherein the microprocessor is further adapted to decompose the electrical impulses received from the transducer into frequency values;
    wherein the microprocessor is further adapted to extract heartbeat frequency values from a predetermined frequency range of about 0.5 to about 5.0 Hz;
    wherein the microprocessor output signal corresponds to the extracted heartbeat frequency values; and
    wherein actuation of the activation control initiates the microprocessor to produce an output signal and the visual display to display the output signal.

10. A stethoscope comprising:
    a sound pickup portion;
    a microprocessor operationally coupled to the sound pickup portion; and
    a visual display portion operationally coupled to the microprocessor;
    wherein the sound pickup portion is adapted to generate a first output signal;
    wherein the microprocessor is adapted to process the first output signal from the sound pickup portion and calculate a rate of rhythmic sounds produced by a patient's heart;
    wherein the microprocessor is further adapted to produce a second electrical output signal corresponding to the rate of rhythmic heart sounds from the sound pickup portion; and wherein the visual display portion is adapted to display an output number corresponding to the second electrical output signal from the microprocessor.

11. The stethoscope of claim 10 further comprising a power source operationally coupled to the microprocessor and to the visual display portion.

12. The stethoscope of claim 10 further comprising an earphone portion operationally coupled to the sound pickup portion.

13. The stethoscope of claim 10 further comprising an activator adapted to actuate the display of the output number.

14. The stethoscope of claim 10 wherein the sound pickup portion further comprises a bell portion and a diaphragm portion.

15. The stethoscope of claim 14 wherein the sound pickup portion further comprises a transducer portion adapted to receive sound energy from the diaphragm and convert it to an electrical output signal for the microprocessor.

16. The stethoscope of claim 10 wherein the microprocessor is further adapted to perform a Fourier transform decomposition on the input signals.

17. The stethoscope of claim 16 wherein the microprocessor is further adapted to sample the input signal, resolve the real time portion of a rhythmic pulse, produce a Fourier transform representing a complete heartbeat cycle, compare the Fourier transform to at least one prestored Fourier transform of an abnormal heartbeat cycle, flag a Fourier transform representing a complete heartbeat cycle matching a stored Fourier transform as abnormal, and send a signal to the display identifying the heartbeat as abnormal.

18. The stethoscope of claim 17 wherein the microprocessor is further adapted to match an abnormal heart beat pattern with at least one known abnormal heart beat pattern types and display the match.

19. The stethoscope of claim 10, further comprising:
 a power source operationally coupled to the microprocessor and to the visual display portion;
 an earphone portion operationally coupled to the sound pickup portion; and
 an activator adapted to actuate the display of the output number;
 wherein the sound pickup portion further comprises a bell portion, a diaphragm portion and a transducer portion adapted to receive sound;
 wherein the microprocessor is further adapted to perform a Fourier transform decomposition on the input signals; and
 wherein the microprocessor is further adapted to sample the input signal, resolve the real time portion of a rhythmic pulse, produce a Fourier transform representing a complete heartbeat cycle, compare the Fourier transform to at least one prestored Fourier transform of an abnormal heartbeat cycle, flag a Fourier transform representing a complete heartbeat cycle matching a stored Fourier transform as abnormal, and send a signal to the display identifying the heartbeat as abnormal; and
 wherein the microprocessor is further adapted to match an abnormal heart beat pattern with at least one known abnormal heart beat pattern types and display the match.

20. A method for measuring a patient's heart rate comprising the steps of:
 a) placing a diaphragm coupled to a bell chamber against a patient's chest;
 b) amplifying the sound of the patient's heart beat in the bell chamber;
 c) channeling a portion of the sound energy to a microprocessor;
 d) transforming the real-time wave data into frequency data;
 e) calculating the heart rate;
 f) producing an electrical output signal corresponding to the calculated heart rate;
and
 g) displaying the heart rate numerically.

21. The method of claim 20 further comprising the steps of:
 channeling a portion of the sound energy to an earphone.

22. The method of claim 20 further comprising the steps of:
 after step a) and before step b),
 channeling a portion of the sound energy to a transducer;
 transducing the sound energy into an electrical signal having the same pattern as the sound energy; and
 sending the electrical signal to the microprocessor.

23. The method of claim 22 further comprising the steps of:
 after step d),
 comparing the Fourier transform of the electrical signal to at least one stored Fourier transform characteristic of a particular heartbeat abnormality;
 identifying a heartbeat corresponding to a Fourier transform matching a stored Fourier transform as abnormal; and
 sending an alarm message to the display corresponding to an abnormal heartbeat.

* * * * *